(12) United States Patent
Shu et al.

(10) Patent No.: US 11,781,153 B2
(45) Date of Patent: Oct. 10, 2023

(54) USE OF OSDGD2β GENE IN BREEDING OF MALE STERILE RICE MATERIALS

(71) Applicant: Zhejiang University, Zhejiang (CN)

(72) Inventors: Qingyao Shu, Zhejiang (CN); Rasbin Basnet, Zhejiang (CN)

(73) Assignee: Zhejiang University, Zhejiang (CN)

( * ) Notice: Subject to any disclaimer, the term of this patent is extended or adjusted under 35 U.S.C. 154(b) by 76 days.

(21) Appl. No.: 17/617,889

(22) PCT Filed: Jul. 3, 2020

(86) PCT No.: PCT/CN2020/100135
§ 371 (c)(1),
(2) Date: Dec. 9, 2021

(87) PCT Pub. No.: WO2021/000936
PCT Pub. Date: Jan. 7, 2021

(65) Prior Publication Data
US 2022/0307049 A1  Sep. 29, 2022

(30) Foreign Application Priority Data

Jul. 3, 2019 (CN) .......................... 201910592941.1

(51) Int. Cl.
*C12N 15/82* (2006.01)

(52) U.S. Cl.
CPC .............................. *C12N 15/8289* (2013.01)

(58) Field of Classification Search
None
See application file for complete search history.

(56) References Cited

U.S. PATENT DOCUMENTS

2010/0143915 A1\* 6/2010 Ronald .............. C12N 15/8245
435/6.14

FOREIGN PATENT DOCUMENTS

| CN | 104313034 A | 1/2015 |
| CN | 108130328 A | 6/2018 |
| CN | 110241126 A | 9/2019 |

OTHER PUBLICATIONS

Baysal, C. et al. Mol Breeding (2016) 36:108. (Year: 2016).\*
"Genbank Accession No. AC139168.1" Genbank Database, Apr. 19, 2003.
"Genbank Accession No. AP014959.I" Genbank Database, Oct. 10, 2015.
Ischebeck T. "Lipids in pollen—They are different," Biochimica et Biophysica Acta-Molecular and Cell Biology of Lipids, vol. 1861. No. 9. Sep. 30, 2016 ISSN: 1388-1981.
GenBank: AC139168.1 Sequence, *Oryza sativa* Japonica Group chromosome 3 clone OJA1364E02, complete sequence, Apr. 19, 2003.
GenBank: AP014959.1 Sequence, *Oryza sativa* Japonica Group DNA, chromosome 3, cultivar: Nipponbare, complete sequence, Oct. 10, 2015.
Gi:27901829, GenBank: AC139168.1, *Oryza sativa* Japonica Group chromosome 3 clone OJA1364E02, complete sequence, Apr. 19, 2003.

\* cited by examiner

*Primary Examiner* — Russell Kallis
(74) *Attorney, Agent, or Firm* — Workman Nydegger (57) ABSTRACT

A new use of OsDGD2β gene in breeding of male sterile rice materials is disclosed. The OsDGD2β gene deletion mutant created by technologies such as CRISPR/Cas9 gene editing is stable in male sterility, with no negative impact on female fertility and other traits (such as photosynthesis), making it uniquely superior in cross breeding and utilization of heterosis.

2 Claims, 4 Drawing Sheets
Specification includes a Sequence Listing.

USE OF OSDGD2β GENE IN BREEDING OF MALE STERILE RICE MATERIALS

CROSS REFERENCE TO RELATED APPLICATION

This patent application claims the benefit and priority of Chinese Patent Application No. 201910592941.1 filed on Jul. 3, 2019, the disclosure of which is incorporated by reference herein in its entirety as part of the present application.

REFERENCE TO SEQUENCE LISTING SUBMITTED ON COMPUTER

The content of the ASCII text file of the sequence listing named "22936-1-SequenceListing.txt" filed concurrently herewith is 9 kb in size with a created date of Dec. 9, 2021, and is being electronically submitted via EFS-Web, is incorporated herein by reference in its entirety.

TECHNICAL FIELD

The present disclosure relates to the technical fields of plant genetic engineering and molecular breeding of rice, and especially relates to the use of OsDGD2β gene in breeding of male sterile rice materials.

BACKGROUND ART

Rice is one of the most important cereals, and more than half of the world's population feed on rice as the staple food. In order to meet the increasing demand for rice yield and quality, the development of male sterility systems has become a continuous demand. Mutations in genes related to anther and pollen development often lead to different forms of male sterility, which is expected to become a useful resource for rice breeding. The heterosis of rice can be achieved by the three-line sterile line of cytoplasmic male sterility (CMS) or the two-line sterile line of photothermosensitive genic male sterility (PTGMS).

However, another new rice breeding system using nuclear male sterility technology to produce hybrid seeds has recently emerged. Lipids and their derivatives are essential for the development and reproduction of pollen anthers. The destruction of lipid synthesis genes may lead to pollen degradation and/or abortion, leading to partial or complete male sterility. It is reported that some genes in rice contribute to the synthesis and secretion of tapetum lipids, such as WDA1, DPW, CYP70B2, Fax1, OsC6, TDR, GAMYB, and so on, which are essential for pollen fertility.

Galactolipids are a large class of higher plant glycerolipids. MGDG and DGDG are two types of galactolipids in all photosynthetic organisms, accounting for 50% and 20% of chloroplast lipids, respectively. These galactolipids are also involved in the development of rice anthers and seeds. In plants, galactolipids are synthesized by adding a galactose derived from UDP-galactose to the diacylglycerol (DAG) backbone to form MGDG via MGDG synthase. Similarly, the second galactose is transferred to MGDG by DGDG synthase to synthesize DGDG.

At present, there are few studies on the OsDGD2β gene, and its function is still unclear.

SUMMARY

The present disclosure provides a use of OsDGD2β gene in breeding of male sterile rice materials. The male sterile OsDGD2β mutant can be applied in rice hybrid breeding and hybrid seed production, and provides resources for breeding male sterile rice materials.

The specific technical solutions are as follows:

The present disclosure provides the use of OsDGD2β gene in breeding of male sterile rice materials. The nucleotide sequence of the OsDGD2β gene is shown as SEQ ID NO: 1; the use is realized by the method of mutating the OsDGD2β gene to make the rice mutant male sterile.

Further, the method is performed by changing the development of rice anthers and pollen through mutating the OsDGD2β gene, resulting in changes in the morphology, size and characteristics of the anthers and pollen, thereby making the rice mutant male sterile.

In the present disclosure, it was found through observation that the osdgdg2β mutant could not fructify in a natural state. Further observations on the morphology of the anthers, pollen and tapetum of the mutant and wild-type rice showed that the anthers of the wild-type rice were bright yellow, the pollen was round, and the color was darker after iodine staining, while the anthers of the osdgdg2β mutant were pale yellow, small, shrunken and curved, with less pollen and no staining. It was also found through microscope observation that in the anthers of the wild-type rice at the flowering stage, the tapetum layer was almost completely degraded. Compared with the wild-type, the pollen of the osdgdg2β mutant was unstained, smaller in volume, shrunken and bending, and the tapetum layer was still a thick monolayer. Through transmission electron microscopy, it was found that wild-type pollen contained starch granules and other components, while mutant pollen did not contain starch granules at all. This proves that the osdgdg2β mutant is male sterile.

In order to further evaluate whether the osdgdg2β mutation has an effect on pistil fertility, the present disclosure artificially emasculated the mutant, covered bags, and then inoculated with wild-type pollen, finding that the hybrid ears of the osdgdg2β mutant could fructify normally, which proved that the osdgdg2β mutant was female fertile.

The above experiment results proved that the osdgdg2β mutant was male sterile and female fertile, and could be used for hybrid breeding and hybrid seed production in the nuclear male sterile system of rice.

In addition, the present disclosure also found through research that in rice, the synthesis of DGDG is coded by five genes, namely OsDGD1α, OsDGD1β, OsDGD1δ, OsDGD2α and OsDGD2β; and OsDGD2β is the only DGDG synthase gene highly expressed in anthers.

The present disclosure also provides a method for breeding male sterile rice varieties, which includes the following steps:

(1) designing the target sequence of the OsDGD2β gene and constructing a CRISPR/Cas9 vector;

(2) constructing a genetically engineered bacteria containing the CRISPR/Cas9 vector in step (1);

(3) transforming the genetically engineered bacteria in step (2) into the callus of mature seeds of rice to obtain a regenerated plants.

Compared with the prior art, the disclosure may have the following beneficial effects:

The embodiments provide a new method to breed male sterile rice materials through OsDGD2β gene mutation. The OsDGD2β gene deletion mutant induced by technologies such as CRISPR/Cas9 gene editing may be stable in male sterility, with no negative impact on female fertility and

BRIEF DESCRIPTION OF THE DRAWINGS

Wherein, Xidao#1 is a wild-type, osdgd2β-1 is a homozygous mutant with a 1-bp deletion, and osdgd2β-2 is a double mutant with a 2-bp deletion and a 5-bp deletion.

A is the two transcripts of the OsDGD2β gene containing the target region.

B is the DNA sequence of the target region containing protospacer adjacent motif (PAM) and the genome-specific sgRNA sequence.

C is the schematic diagram of the mutant truncated protein, and Glycos_transf_1 represents the unique domain.

in which, A, B and C is the fructification of wild-type Xidao #1, the mutant osdgd2β-1, and the osdgd2β-1 aborted mutant 15 days after receiving wild-type pollination, respectively.

in which, Xidao#1 is a wild type, osdgd2β-1 is a homozygous mutant with a 1-bp deletion, and osdgd2β-2a is a double mutant with simultaneous 2-bp deletion and 5-bp deletion.

in which, Xidao#1 is a wild type, osdgd2β-1 is a homozygous mutant with a 1-bp deletion, and osdgd2β-2a is a double mutant with simultaneous 2-bp deletion and 5-bp deletion.; E represents epidermis, T represents tapetum, and P represents pollen.

in which, A is the leaf and B is the anther; OsDGD1α, OsDGD1β, OsDGD1δ, OsDGD2α and OsDGD2β are synthetic genes of DGDG in rice.

DETAILED DESCRIPTION OF THE EMBODIMENTS

The present disclosure will be further described below in combination with specific embodiments. The following are only specific embodiments of the present disclosure, but the protection scope of the present disclosure is not limited thereto.

EXAMPLE 1

Construction and Identification of the Mutants

1. Construction of the Mutants

The CRISPR vector pHUN4c12 was used to construct a genome editing vector targeting OsDGD2β mutation. A specific target sequence targeting the third exon of OsDGD2β was designed by CRISPR-P 1.0 (genome specific sgRNA sequence: AGGTCAATAGTTTGCAATG, as shown in SEQ ID NO. 2), and then synthesized an oligonucleotide chain (D2b-T/-B) (D2b-T: GGCACATTGCAAACTAT-TGACCT, as shown in SEQ ID NO. 3, D2b-B: AAACAGGTCAATAGTTTGCAATG, as shown in SEQ ID NO. 4); bound the oligonucleotide strands using annealing buffer, digested the pHUN4c12 vector with BsaI-HF (NEB), and ligated the oligonucleotide double strands with T4 ligase. The ligated vector was named pHUN4c12s:OsDGD2 and transformed into DH5 E. coli competent. The inserted sgRNA was verified by sequencing primer (seq-F): GCC-CATTACGCAATTGGACG, as shown in SEQ ID NO.5.

Figure 1:
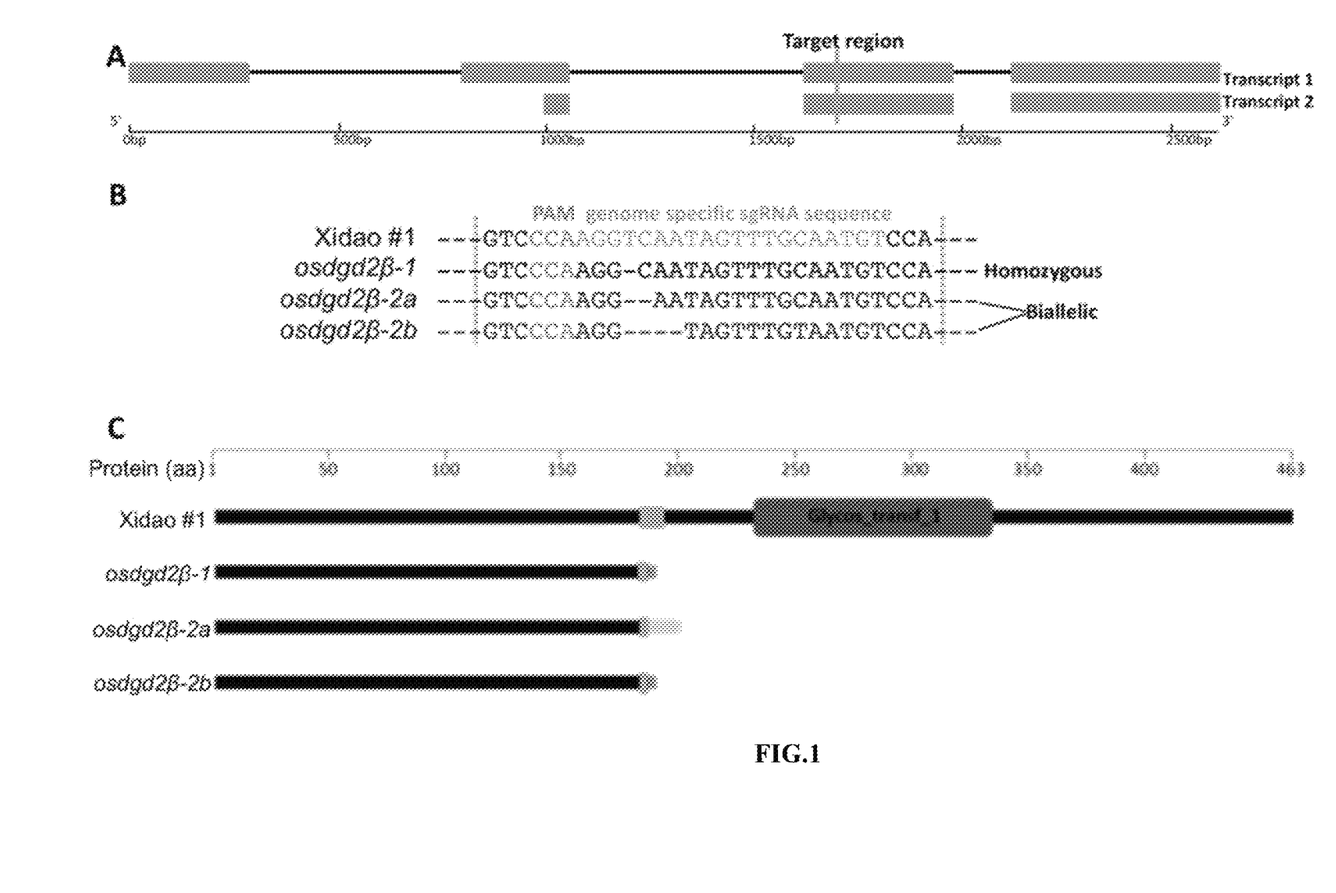
FIG. 1 is the target mutation of OsDGD2β using the CRISPR/Cas9 system in example 1.

The recombinant vector was transferred to Agrobacterium (EHA105), and further transferred to the mature seed callus of the japonica rice variety Xidao#1 using the Agrobacterium-mediated method. The recombinant vector was inserted into the plant genome and expressed to produce sgRNA and Cas9 nucleic acid. The enzyme was guided by the pairing of sgRNA and the target sequence, so that the targeted plant genome would be cleaved by Cas9 nuclease to produce double-strand breaks. Errors occurred in the genome repair process, resulting in two osdgd2β mutants (osdgd2β-1, osdgd2β-2) (as shown in FIG. 1).

2. Identification of the Mutants

The leaf DNA of osdgd2β mutant was extracted by CTAB method, using PCR primers D2b-F/-R (D2b-F: TCAAGT-TATGGCATTTTCCGTCT, as shown in SEQ ID NO. 6, D2b-R: GCACCCTTGAAGAATGCTTGT, as shown in SEQ ID NO. 7), to amplify and sequence the target region of the transformed plant.

The target fragment of the biallelic mutant osdgd2β-2 was cloned into the pGEM-T vector, transformed into E. coli, and verified by sequencing. The protein sequence was analyzed with ExPASy (http://web.expasy.org/translate/) translation tool. The $T_0$ generation mutant plant was planted, and the tillers were separately planted after flowering for subsequent research.

EXAMPLE 2

The Phenotypic Characteristics of the Mutant

1. Study of Anther Structure and Pollen Fertility

Figure 2:
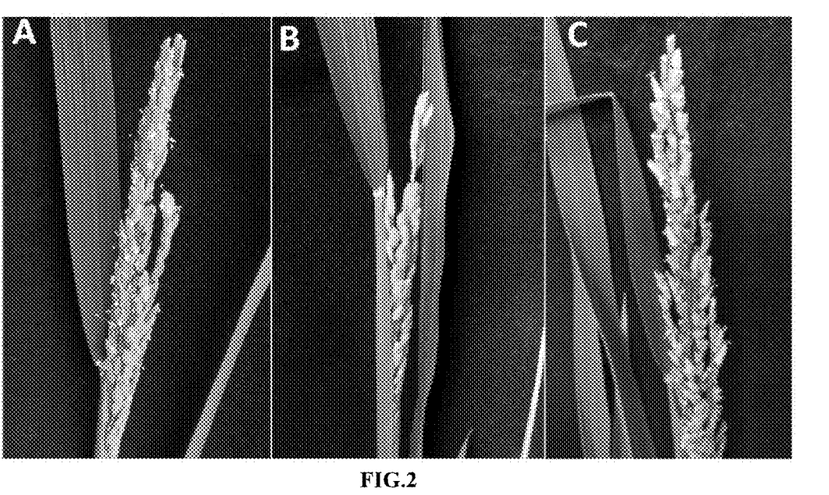
FIG. 2 is a comparison of rice panicles of wild type Xidao #1 (A) and mutant osdgd2β-1 (B) on the day of flowering in example 2.

On the day of heading of the $T_0$ generation mutant osdgd2β and the wild type, the small hoop was collected and added to a centrifuge tube with the fixative FAA (10 ml formalin (37% formaldehyde)/5 ml 100% acetic acid/50 ml 95% alcohol/35 ml water, for 100 ml solution), and stored at room temperature. The flower and anther structure of mutant osdgd2 β and wild-type were observed under an ordinary microscope, and the pollen fertility stained with 1% IKI was observed under a compound microscope. As shown in FIG. 2, the mutant sheath panicles were not completely exposed compared to the wild type during the flowering period. Moreover, compared with the wild type at flowering, the anthers of most spikelets in the mutants were not exposed (FIG. 2B). In addition, in order to evaluate whether the mutant affected pistil fertility, the mutant was emasculated, and then the wild type was used as the male parent to cross. The results showed that these hybrid ears could fructify normally, and the mutants were female fertile (FIG. 2C).

Figure 3:
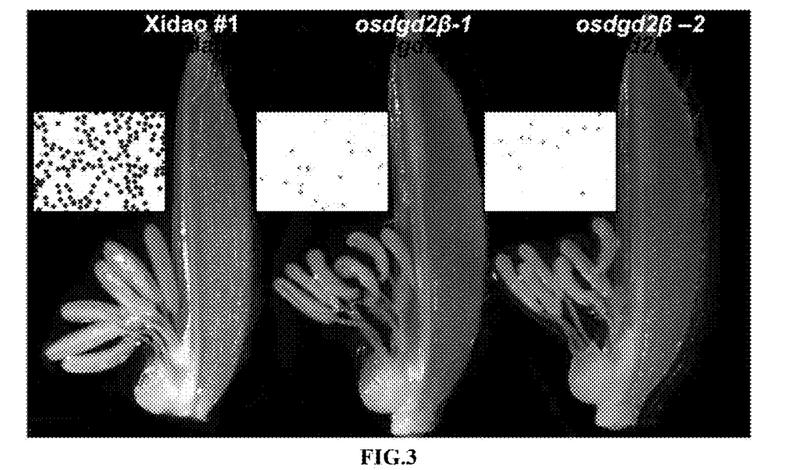
FIG. 3 is a diagram of the observation of the difference in the anthers of the depleted sclerotium by 1% IKI pollen staining in example 2.

Microscope results showed (as shown in FIG. 3) that the anthers and pollen of the mutant had lighter staining, and were smaller in size and shrunken compared with the wild type (osdgd2β-1 and osdgd2β-2 in FIG. 3). In the wild type, the tapetum layer is almost completely degraded (Xidao #1 in FIG. 3); in the mutant, the tapetum layer is still a thick monolayer (osdgd2β-1 and osdgd2β-2 in FIG. 3).

2. Slicing

The anthers of two mutant osdgd2β and wild-type were sliced and observed by transmission electron microscope (TEM). The specific steps are as follows:

The anthers of the two mutant osdgd2β and wild type were soaked in 2.5% glutaraldehyde phosphate buffered saline (PBS, 0.1 M pH 7.0) for more than 4 hours, fixed with 1% osmium tetroxide for more than 2 hours, and then rinsed with PBS. The anthers were dehydrated with gradient ethanol (30%, 50%, 70%, 80%, 90%, 95% and 100%) firstly, then pure acetone, and finally lilac resin, cut with a ultra-microtome with glass knives into 2 μm semi-thin slices, stained with 0.5% toluidine blue, and observed under a microscope. The 100 nm ultra-thin slices were obtained with LEICA EM UC7U microtome, stained with uranyl acetate and alkaline lead citrate for 5-10 minutes, and observed under a transmission electron microscope.

Figure 4:
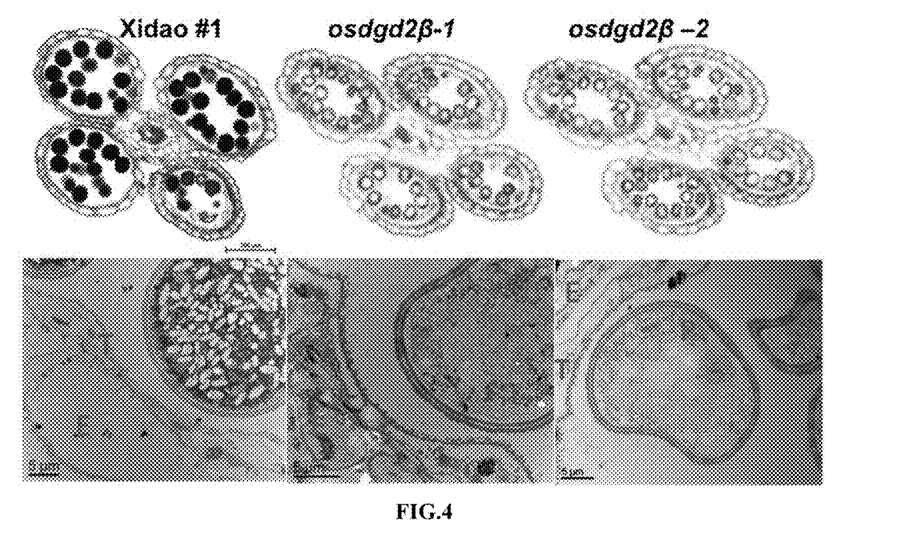
FIG. 4 is the observation of a cross section of the anther stained with 0.5% toluidine blue under microscope (top) and the one enlarged 4000× under a transmission electron microscope (bottom) in example 2.

The observation of pollen grains under transmission electron microscope showed that wild-type pollen contained starch grains and other components (Xidao #1 in FIG. 4), while mutant pollen had no starch grains (osdgd2β-1 and osdgd2β-2 in FIG. 4); The tapetum in the mutant anthers showed a delay in programmed cell death.

EXAMPLE 3

Gene Expression Analysis

The leaves and anthers of mutant osdgd2β and wild-type were collected on the day of flowering, total RNA of which was extracted with RNA extraction kit, and reverse transcripted with reverse transcription kit. qRT-PCR test was performed with Hieff™ qPCR SYBR® reaction mixture.

The experiment was carried out by three biological and three technical replicates. OsActin was used as an internal reference (Li et al., (2007) Genome-wide analysis of the phospholipase D family in Oryza sativa and functional characterization of PLDb1 in seed germination, Cell Research 17:881-894), and the relative expression levels of genes were calculated by the $2^{-\Delta\Delta Ct}$ method. The primers are shown in Table 1.

TABLE 1

| Primer name | Primer sequence |
| --- | --- |
| D1a-RT-F | AAGGGACCATGCAGATGACTCAC<br>As shown in SEQ ID NO. 8 |
| D1a-RT-R | ACGAACTCCTCCGGGGTCCT<br>As shown in SEQ ID NO. 9 |
| D1b-RT-F | AGTTGTGGATGGGGACTGG<br>As shown in SEQ ID NO. 10 |
| D1b-RT-R | TCACCAGCCATATACAGGGTGT<br>As shown in SEQ ID NO. 11 |
| D2a-RT-F | CCGTGAAGGTTCACCCAGGA<br>As shown in SEQ ID NO. 12 |
| D2a-RT-R | GCGGCAATTAGGGAACTGCT<br>As shown in SEQ ID NO. 13 |
| D2b-RT-F | TGGAGCTGTATGGCAGTGGA<br>As shown in SEQ ID NO. 14 |
| D2b-RT-R | TCGCCAAAGCTTCTGCAGTT<br>As shown in SEQ ID NO. 15 |
| D1d-RT-F | TGAGGTGCAATCAGCGGCTA<br>As shown in SEQ ID NO. 16 |
| D1d-RT-R | TTCGCGACAAAGTCCTCCGA<br>As shown in SEQ ID NO. 17 |
| D2b-F | TCAAGTTATGGCATTTTCCGTCT<br>As shown in SEQ ID NO. 18 |
| D2b-R | GCACCCTTGAAGAATGCTTGT<br>As shown in SEQ ID NO. 19 |
| Actin-F | GAACTGGTATGGTCAAGGCTG<br>As shown in SEQ ID NO. 20 |
| Actin-R | ACACGGAGCTCGTTGTAGAAG<br>As shown in SEQ ID NO. 21 |

Figure 5:
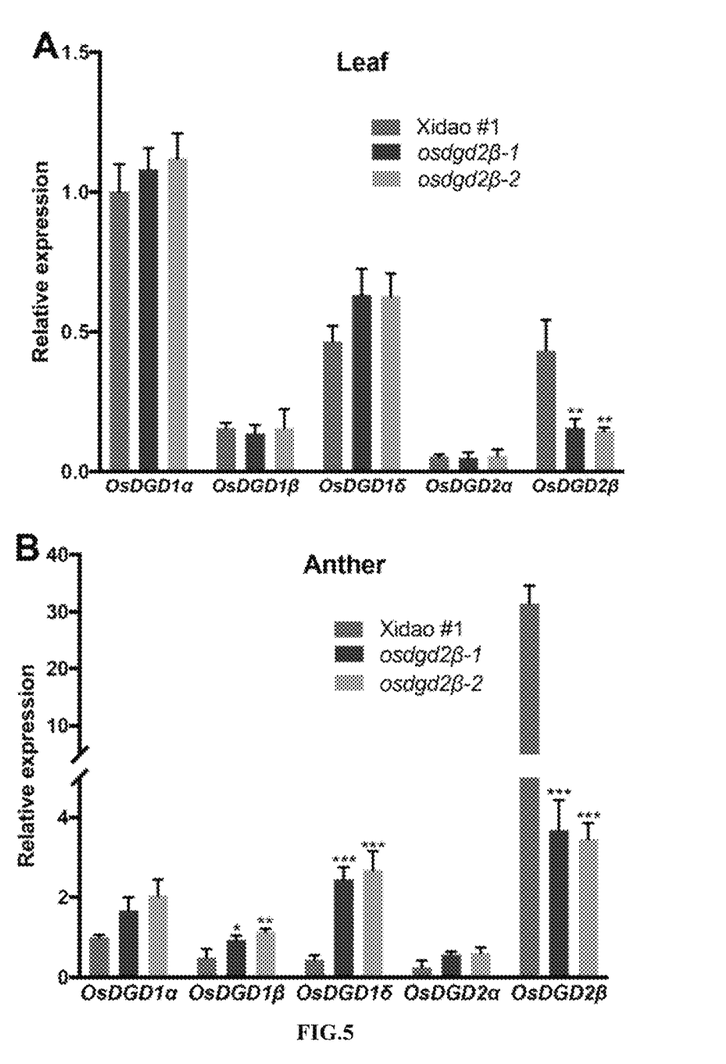
FIG. 5 is the relative expression levels of DGDG synthesis genes in the leaves and anthers of wild-type Xidao#1, mutants osdgd2β-1 and osdgd2β-2 in example 3.

As shown in FIG. 5, OsDGD2β in the leaves and anthers of the mutants was significantly reduced by about 65.26% and 88.62%, respectively. The other DGDG synthesis genes in the leaves were not significantly different from those of the wild type (FIG. 5A), whereas in the anthers, except for OsDGD2α, all of which were significantly different from those in the wild type (FIG. 5B). In the two mutants osdgd2β, the expression levels of OsDGD1δ, OsDGD1β and OsDGD1α0 increased by 5.9-fold, 2.1-fold and 1.8-fold, respectively.

What is claimed is:

1. A method for generating a male sterile rice plant, the method comprising:
   (i) constructing a recombinant CRSPR/Cas9 knockout vector that targets the OsDGD2β gene of SEQ ID NO:1;
   (ii) transferring the recombinant CRSPR/Cas9 knockout vector into Agrobacterium; and
   (iii) transforming a rice with the Agrobacterium to obtain a male sterile rice plant.

2. The method according to claim 1, wherein an sgRNA for the recombinant CRSPR/Cas9 knockout vector is set forth in SEQ ID NO:2.

* * * * *

SEQUENCE LISTING

```
<160> NUMBER OF SEQ ID NOS: 21

<210> SEQ ID NO 1
<211> LENGTH: 3676
<212> TYPE: DNA
<213> ORGANISM: Artificial Sequence
<220> FEATURE:
<223> OTHER INFORMATION: DNA sequence of OsDGD2-beta gene
```

-continued

```
<400> SEQUENCE: 1
tgacggcaac ctccacaccc aacggccaaa cctgaaacgc catccactcc acggcaccag      60
gctccccctt ctccctcctc tccgcctcct cccatccaca tccgcggccg cgccgatcgc     120
acaggtaacc agctcctccc ctcccccttcc cctcgccggg ttcctcccac ccgcgcgctg    180
tcctggaacc gcgattagga tctcgagctg ggcgggttga gtttgaatcg ccggtgggta     240
gggttggaat tagatcgatg ctgcggtcat gctggatctc tctgttttag cccccccgagt   300 gttcgtgaat cacggctgca tgttggtggg cgccgaatta gatgctccct ggattctctg    360
tttttcttta agaaaaaaaa tatccccaag agatgattcg attctccatg cgtatgggcg    420
ggataagggg gaaaaatgat ggcacggctt tgcgggatgc cggcattgtt ctttggccac    480
ttgtaatggt acgctttggc gatgtgattt aagggctggt ggggtggtgc ttgttggtca    540
tttcagcagc tttgtgcggt cggggtggtc tcggtgccga tggcgaggaa gcagcatatc    600
gccatattca ccacggcgag cctgccatgg atgactggaa ctgccgtcaa cccctcttc     660 cgagcggcct acctcgcgaa ggccgggac tgggaggtta cgctggtggt tccatggctt     720
tcgaaggggg accagctgct ggtttatcct aacaagatga aattcagtgt gcccggggag    780
caagaaggct atgtgcgacg gtggctcgag gagcgaattg ggctgctgcc gaagtttgag    840
ataaaattct atcctggaaa ggtaaagtaa accaaaattt ccaaagtact gtatagttct    900
atctgatatt atcatgatct aaatgtaatg tcaaagtgaa tggcgtggta cggtttattg    960
cttgtttgat atgatgcttc tgattttccc atggttcgca aaaattcatc acacagttga   1020
gtttaaattg cttggccata cagttgtaca cactacacac gttgctctta gctcatgtta   1080
gtgtcaaaac taaatggag caggattgta tgttctgatt cttgttgaga tttgagaagc    1140
aaatccaata aaccgtagaa gttggttctt tttttaaaa aaatgcatgc atctagtacc    1200
ttcaacacaa gaattactag aaatatctat ggtagtggag tgagcagaaa atgagacact   1260
gagtgttata aaacttgaaa ggccagtata agttgagcgg gtggtcatgt ggttgatgtt   1320
cttgtgatgt cataatgagg ttgattgaca tattttctcc ccatacagtt ctcaacggag    1380
aaaagaagca ttctacctgc tgggacatc acccagactg tatctgatga taaagcagac    1440
attgcagttc ttgaagagcc agagcatctt acatggtacc atcatggacg aaggtggaaa    1500
aacaaattca gaaagttat aggtgttgtt cataccaact atttggagta tgtcaagaga    1560
gagagaaatg gatatatcca tgcatttctc ttaaaacata tcaattcctg ggtcactgac   1620
atctactgcc ataaggttag caccttcaat ttctattata tttttctggg tttgcatgtt    1680
tttgaagttc ttttctattc tattttgctg gtttgcatat tttaaagtt tttcagtagt    1740 tcaactatga acatctcaat ttgcttcata taaccttata agtctcctgt ctcagtaata    1800
cccttcatcc ttgatggcaa aatatgttct taacatggat atgattcttt gctctttgga    1860
cgtatgtgac attgcctaac ttctagaagt tcattaccag ctgttgtatg acattagtct    1920
atgaaatgaa cagctgtgat atgcctccat catgcatgga atcaccatgt tcgcatagtg    1980
accagataaa tattgccatt ttttgaataa agttaaggat gttccacata ttatgcacag    2040
tatgatgccg aatggcataa aaacctttgt aatgtatcca tatttattta aataatgaga    2100
gcttgagaat ttattcttat caagttatgg cattttccgt ctataatttg atatgtaatc    2160 atgtgctttα ttttatctt tcattgttat ttcttttgta ggttataaga ttatcagcag     2220
caactcagga agtcccaagg tcaatagttt gcaatgtcca tggagtaaat ccaaaattta    2280
ttgaaattgg taaactgaag catcagcaga tatctcaaag agaacaagca ttcttcaagg    2340
```

```
gtgcatatta tattggaaag atggtctgga gtaaaggtta tacagaacta ctccagctgc    2400
ttcagaagca ccagaaggaa ttatctggtc ttaagatgga gctgtatggc agtggagaag    2460
attctgatga ggttaaagca tcagccgaga aactaaatct tgatgttcga gtctatcctg    2520
gtcgtgacca tggagattcc atatttcatg agtgagtact tagcagaaaa gtaatggttt    2580
aaatgttatt cacaagcaat ttagctgcta gattgtattt tgggctatgt ttttattaga    2640
agtgatttat gttattgatt tacttatgat ctaactgaat tttgttatct ccttttcagc    2700
tacaaggttt tcataaaccc aagcaccaca gatgtggtat gcacgacaac tgcagaagct    2760
ttggcgatgg ggaaaattgt gatatgtgca accatcctt cgaatgaatt cttcaaaagg     2820
tttcctaact gccacatgta caatactgag aaagagtttg tgagattgac tatgaaagca    2880
ttggctgaag agccaatccc actgtcagag gaactgagac atgagctttc ctggaggca    2940 gcaacagaga gatttgtcag ggttgctgat attgcaccaa tcatgtctat caagcagcat    3000
tctccctctc cccagtattt catgtatata tctccagatg aactgaagaa gaacatggag    3060
gaggcgtcgg catttttca taatgcgatt tctgggtttg aaacggcccg ttgtgttttt     3120
ggtgccatac cgaatactct gcagcctgat gaacagcaat gcaaggaact tggctggagg    3180
ctccaggaat gacagtcatt tcttcccacg ctgttgtcaa tgacaataga atgccaacta    3240
acagcccagg gaacttggct tggggaacta actacgtaac gcaattatct tttgctccaa    3300
aactacgaag gactgaacag acaagggtga ttccttgtttt ctgctatggt ggtacactgg   3360
tattgcaatt ctccttcaca attgtggagt gtccatcaga catcagttac tgtaatgcat    3420
catatcttgg aattgtaaat gtgcggcagt tgaagtgatt accaatgctg tcttttcatg    3480
tagcctgtgt aatgtaaagc ttactgttgc ttcccgagtt tggcacaatt ttaaagatat    3540
cttgtctggt gtttcacaac catttttgtt ggcgtgctgc tgctccttt ccaattaaaa     3600 atgatcattg tatccttgta ttcctgtcat cctgtgtgcc acttgataga aataacttg     3660 ccttctggga cttagg                                                    3676
```

<210> SEQ ID NO 2
<211> LENGTH: 19
<212> TYPE: DNA
<213> ORGANISM: Artificial Sequence
<220> FEATURE:
<223> OTHER INFORMATION: DNA sequence of the genome specific sgRNA

<400> SEQUENCE: 2

```
aggtcaatag tttgcaatg                                                 19
```

<210> SEQ ID NO 3
<211> LENGTH: 23
<212> TYPE: DNA
<213> ORGANISM: Artificial Sequence
<220> FEATURE:
<223> OTHER INFORMATION: DNA oligonucleotide chain D2b-T

<400> SEQUENCE: 3

```
ggcacattgc aaactattga cct                                            23
```

<210> SEQ ID NO 4
<211> LENGTH: 23
<212> TYPE: DNA
<213> ORGANISM: Artificial Sequence
<220> FEATURE:
<223> OTHER INFORMATION: DNA oligonucleotide chain D2b-B -continued

```
<400> SEQUENCE: 4
aaacaggtca atagtttgca atg                                          23

<210> SEQ ID NO 5
<211> LENGTH: 20
<212> TYPE: DNA
<213> ORGANISM: Artificial Sequence
<220> FEATURE:
<223> OTHER INFORMATION: sequencing primer (seq-F)

<400> SEQUENCE: 5
gcccattacg caattggacg                                              20

<210> SEQ ID NO 6
<211> LENGTH: 23
<212> TYPE: DNA
<213> ORGANISM: Artificial Sequence
<220> FEATURE:
<223> OTHER INFORMATION: forward primer D2b-F

<400> SEQUENCE: 6
tcaagttatg gcattttccg tct                                          23

<210> SEQ ID NO 7
<211> LENGTH: 21
<212> TYPE: DNA
<213> ORGANISM: Artificial Sequence
<220> FEATURE:
<223> OTHER INFORMATION: reverse primer D2b-R

<400> SEQUENCE: 7
gcacccttga agaatgcttg t                                            21

<210> SEQ ID NO 8
<211> LENGTH: 23
<212> TYPE: DNA
<213> ORGANISM: Artificial Sequence
<220> FEATURE:
<223> OTHER INFORMATION: forward primer D1a-RT-F

<400> SEQUENCE: 8
aagggaccat gcagatgact cac                                          23

<210> SEQ ID NO 9
<211> LENGTH: 20
<212> TYPE: DNA
<213> ORGANISM: Artificial Sequence
<220> FEATURE:
<223> OTHER INFORMATION: reverse primer D1a-RT-R

<400> SEQUENCE: 9
acgaactcct ccggggtcct                                              20

<210> SEQ ID NO 10
<211> LENGTH: 20
<212> TYPE: DNA
<213> ORGANISM: Artificial Sequence
<220> FEATURE:
<223> OTHER INFORMATION: forward primer D1b-RT-F

<400> SEQUENCE: 10
agttgtggat ggggactgg                                               20
```

```
<210> SEQ ID NO 11
<211> LENGTH: 22
<212> TYPE: DNA
<213> ORGANISM: Artificial Sequence
<220> FEATURE:
<223> OTHER INFORMATION: reverse primer D1b-RT-R

<400> SEQUENCE: 11
tcaccagcca tatacagggt gt                                              22

<210> SEQ ID NO 12
<211> LENGTH: 20
<212> TYPE: DNA
<213> ORGANISM: Artificial Sequence
<220> FEATURE:
<223> OTHER INFORMATION: forward primer D2a-RT-F

<400> SEQUENCE: 12
ccgtgaaggt tcacccagga                                                 20

<210> SEQ ID NO 13
<211> LENGTH: 20
<212> TYPE: DNA
<213> ORGANISM: Artificial Sequence
<220> FEATURE:
<223> OTHER INFORMATION: reverse primer D2a-RT-R

<400> SEQUENCE: 13
gcggcaatta gggaactgct                                                 20

<210> SEQ ID NO 14
<211> LENGTH: 20
<212> TYPE: DNA
<213> ORGANISM: Artificial Sequence
<220> FEATURE:
<223> OTHER INFORMATION: forward primer D2b-RT-F

<400> SEQUENCE: 14
tggagctgta tggcagtgga                                                 20

<210> SEQ ID NO 15
<211> LENGTH: 20
<212> TYPE: DNA
<213> ORGANISM: Artificial Sequence
<220> FEATURE:
<223> OTHER INFORMATION: reverse primer D2b-RT-R

<400> SEQUENCE: 15
tcgccaaagc ttctgcagtt                                                 20

<210> SEQ ID NO 16
<211> LENGTH: 20
<212> TYPE: DNA
<213> ORGANISM: Artificial Sequence
<220> FEATURE:
<223> OTHER INFORMATION: forward primer D1d-RT-F

<400> SEQUENCE: 16
tgaggtgcaa tcagcggcta                                                 20

<210> SEQ ID NO 17
<211> LENGTH: 20
<212> TYPE: DNA
<213> ORGANISM: Artificial Sequence
<220> FEATURE:
<223> OTHER INFORMATION: reverse primer D1d-RT-R
```

```
<400> SEQUENCE: 17
ttcgcgacaa agtcctccga                                                   20

<210> SEQ ID NO 18
<211> LENGTH: 23
<212> TYPE: DNA
<213> ORGANISM: Artificial Sequence
<220> FEATURE:
<223> OTHER INFORMATION: forward primer D2b-F

<400> SEQUENCE: 18
tcaagttatg gcattttccg tct                                               23

<210> SEQ ID NO 19
<211> LENGTH: 21
<212> TYPE: DNA
<213> ORGANISM: Artificial Sequence
<220> FEATURE:
<223> OTHER INFORMATION: reverse primer D2b-R

<400> SEQUENCE: 19
gcacccttga agaatgcttg t                                                 21

<210> SEQ ID NO 20
<211> LENGTH: 21
<212> TYPE: DNA
<213> ORGANISM: Artificial Sequence
<220> FEATURE:
<223> OTHER INFORMATION: Primer Actin-F

<400> SEQUENCE: 20
gaactggtat ggtcaaggct g                                                 21

<210> SEQ ID NO 21
<211> LENGTH: 21
<212> TYPE: DNA
<213> ORGANISM: Artificial Sequence
<220> FEATURE:
<223> OTHER INFORMATION: Primer Actin-R

<400> SEQUENCE: 21
acacggagct cgttgtagaa g                                                 21
```